(12) United States Patent  (10) Patent No.: US 7,828,257 B2
Leonard  (45) Date of Patent: Nov. 9, 2010

(54) ANESTHESIA EQUIPMENT LIFT SYSTEM

(75) Inventor: Robert Dean Leonard, Fallbrook, CA (US)

(73) Assignee: Intellivet Anesthesia Equipment, LLC, Gardnerville, NV (US)

( * ) Notice: Subject to any disclaimer, the term of this patent is extended or adjusted under 35 U.S.C. 154(b) by 1007 days.

(21) Appl. No.: 11/586,239

(22) Filed: Oct. 25, 2006

(65) Prior Publication Data

US 2007/0093784 A1   Apr. 26, 2007

Related U.S. Application Data

(60) Provisional application No. 60/730,487, filed on Oct. 26, 2005.

(51) Int. Cl.
| | |
|---|---|
| *E04G 3/00* | (2006.01) |
| *A47F 5/00* | (2006.01) |
| *A47F 7/00* | (2006.01) |
| *F16M 11/00* | (2006.01) |
| *F16M 13/00* | (2006.01) |
| *A47J 47/16* | (2006.01) |
| *B66B 9/02* | (2006.01) |
| *B66B 9/04* | (2006.01) |

(52) U.S. Cl. .............. 248/274.1; 248/124.1; 248/125.1; 248/132; 248/161; 187/267; 187/273

(58) Field of Classification Search ............. 248/274.1, 248/124.1, 125.1, 132, 161; 187/267, 273
See application file for complete search history.

(56) References Cited

U.S. PATENT DOCUMENTS

| RE32,052 | E | * | 12/1985 | Rosenberg et al. | .......... 119/756 |
| 5,217,090 | A | * | 6/1993 | Billington et al. | ........... 182/141 |
| 5,469,492 | A | * | 11/1995 | Burbury et al. | .............. 378/197 |
| 5,586,816 | A | * | 12/1996 | Geiss, II | ...................... 312/301 |
| 5,702,222 | A | * | 12/1997 | Rosen | ......................... 414/228 |
| 2001/0040233 | A1 | * | 11/2001 | Chamberlain | ................ 254/4 R |
| 2005/0109892 | A1 | * | 5/2005 | Bober et al. | .............. 248/125.2 |

* cited by examiner

*Primary Examiner*—Anita M King
*Assistant Examiner*—Christopher Garft
(74) *Attorney, Agent, or Firm*—Craig R. Miles; CR Miles, P.C.

(57) ABSTRACT

An anesthesia equipment lift which couples to a table to provide an anesthesia equipment mount surface coupled to a lift element which travels from a first location to a second location to position mounted inhalation anesthesia equipment proximate to a patient located on the table surface to perform inhalation anesthesia.

8 Claims, 5 Drawing Sheets

ANESTHESIA EQUIPMENT LIFT SYSTEM

This United States Non-provisional Patent Application claims the benefit of U.S. Provisional Patent Application No. 60/730,487, hereby incorporated by reference herein.

I. BACKGROUND

An anesthesia equipment lift which couples to a table to provide an anesthesia equipment mount surface coupled to a lift element which travels from a first location to a second location to position mounted inhalation anesthesia equipment proximate to a patient located on the table surface to perform inhalation anesthesia.

Inhalation anesthesia equipment must be located proximate to the patient on the treatment table during inhalation anesthesia. In conventional practice, the anesthesia equipment may be mounted at fixed location proximate to the table surface. As such, during periods in which the anesthesia equipment is not being utilized for inhalation anesthesia, the anesthesia equipment can be an impediment to utilizing the treatment table for other procedures and makes the anesthesia equipment exposed and susceptible to damage by contact. Alternately, the anesthesia equipment may be coupled to a movable platform, which allows the anesthesia equipment to be moved distal from the treatment table. However, this may not make the anesthesia equipment less susceptible to damage and only serves to place the anesthesia equipment at a less convenient location for subsequent use.

With respect to using anesthesia equipment, the present invention discloses technology which addresses each of the above-mentioned problems in a practical fashion.

II. SUMMARY OF THE INVENTION

Accordingly, a broad object of the invention can be to provide a lift which can be coupled to a table (such as a veterinary treatment table or anesthesia treatment table or other type of treatment table) which includes a lift panel having a mounting surface (or mount surface) on which at least part of an anesthesia device or anesthesia equipment can be coupled and such lift panel travels vertically from a first location to a second location to position at least a part of the lift panel at a greater height than the top table surface such that mounted inhalation anesthesia equipment can be proximate to a patient located on the table surface to perform inhalation anesthesia.

A second broad object of the invention can be to provide a lift including the above-described lift panel which couples to a treatment table and further operates to travel a a sufficient distance horizontally from a storage position beneath the bottom table surface to a location at which the lift panel can then operate as above-described to travel a distance vertically to establish at least a part of the lift panel at a height greater than the table top surface such that anesthesia equipment coupled to the mount surface of the lift panel can provide inhalation anesthesia to a patient located on the table surface.

Naturally, further objects of the invention are disclosed throughout other areas of the specification and drawings.

III. A BRIEF DESCRIPTION OF THE DRAWINGS

IV. DETAILED DESCRIPTION OF THE PREFERRED EMBODIMENTS

An anesthesia equipment lift which couples to a table having an anesthesia equipment mount surface coupled to a lift element which travels from a first location to a second location to position mounted inhalation anesthesia equipment proximate to a patient located on the table surface to perform inhalation anesthesia.

Figure 1:
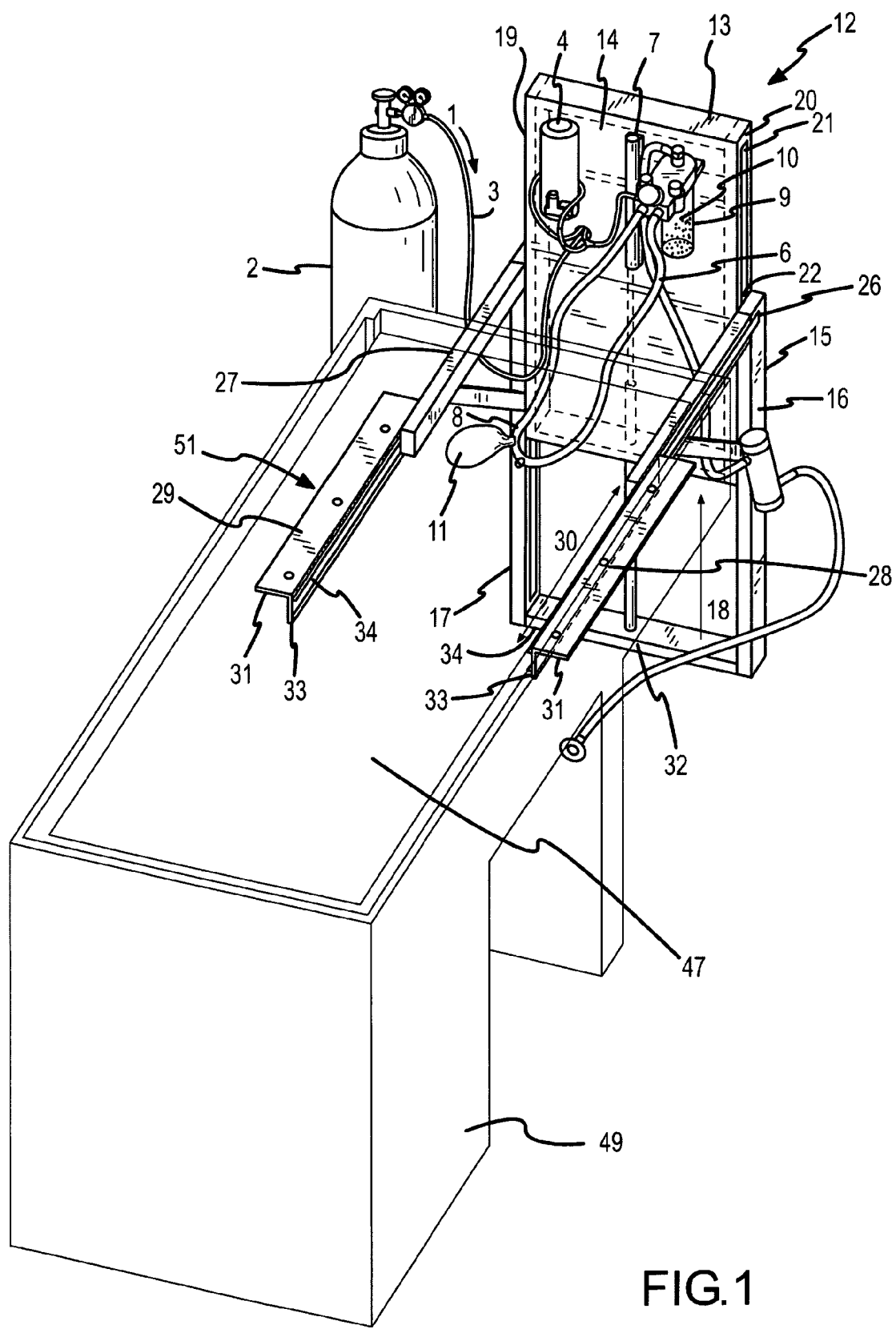
FIG. 1 is a perspective view of an embodiment of the anesthesia equipment lift invention positioned to provide inhalation anesthesia to a patient located on the table surface.

Referring primarily to FIG. 1, a flow of gas (1) can be generated by release of an amount of gas from a pressure regulated compressed gas cylinder (2)(or other type of pressure regulated device) into a gas flow conduit (3) coupled to an anesthetic vaporizer (4). The anesthetic vaporizer (4) contains an amount of the anesthetic and can be adjusted to deliver more or less of the anesthetic to a patient through an inhalation circuit (6). The volume of gas introduced into inhalation circuit (6) can be assessed by observation of a gas flow meter (7) coupled to the flow of gas (1) entering the inhalation circuit (6). The patient inhales the gas in the inhalation circuit (6) and a portion of the entrained anesthetic is transferred into the patient's blood stream. The portion of the anesthetic which does not enter the patient's blood stream can be exhaled into an exhalation circuit (8). The exhaled mixture of gases within the exhalation circuit (8) including the remaining amount of entrained anesthetic may be transferred to a canister (9) containing an amount of carbon dioxide absorbent (10). The carbon dioxide in the exhalation gases can be absorbed by the carbon dioxide absorbent (10) and the resulting mixture of gases can be returned to the inhalation circuit (6). The amount of anesthetic in the gas mixture returned to the inhalation circuit (6) can be adjusted by introduction of an additional amount of anesthetic from the anesthetic vaporizer (4) or introduction of oxygen (or other partial pressures of gases) from the compressed gas cylinder (2) as necessary to maintain inhalation anesthesia. A flexible breathing bag (11) accommodates the respiratory volume of the patient. A pressure relief valve can be provided for release of the mixture of gases from the inhalation and exhalation circuits (6)(8) to maintain the desired gas pressure within the re-breathing circuit. The anesthetic vaporizer (4), the gas flow meter (7), the canister (9) and other parts of the anesthetic delivery device along with the conduits which fluidicly connect the various components can each or all be included as part of an anesthesia treatment device referred to herein.

Again referring primarily to FIG. 1, the invention can further include an anesthesia equipment lift system (12)(which can be coupled to a table (49)) which provides a lift panel (13)

having at least one anesthesia equipment mount surface (14) (or mount surface) to which at least part of an anesthesia treatment device as above-described, or other types or kinds of anesthesia equipment, can be mounted. Depending upon the configuration of the anesthesia equipment to be mounted to the anesthesia equipment mount surface (14), a variety of mechanical fasteners, such as bolts and nuts having mated spiral threads, screws, rivets, or the like, can be used to secure the components of the anesthesia equipment to the anesthesia equipment mount surface (14). The anesthesia treatment device or parts thereof and the method of using the anesthesia treatment device above-described is not intended to be limiting with respect to the numerous and varied kinds and types of anesthesia devices or anesthesia equipment (or other types of equipment or devices) that can be mounted to the anesthesia mount surface (14) nor is the description intended to limit the configuration of the anesthesia equipment or limit the invention to any particular method of inhalation anesthesia. Rather the illustrative example provides a sufficient description for those skilled in the art of inhalation anesthesia to mount the numerous and varied types of anesthesia treatment devices or parts thereof to the anesthesia equipment mount surface (14) in various configurations to allow inhalation anesthesia to be performed.

Figure 2:
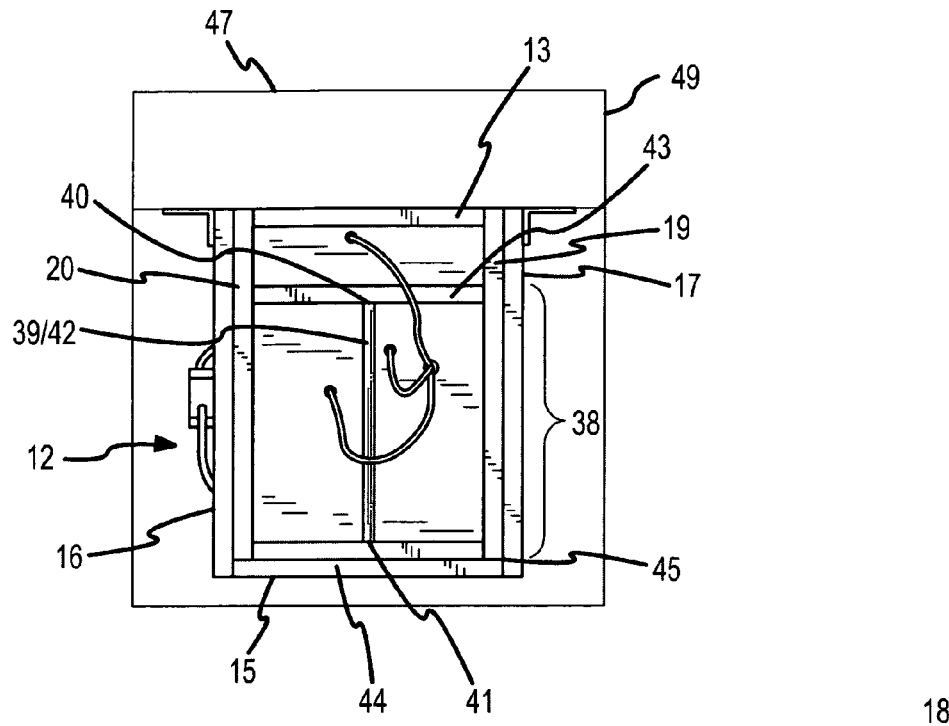
FIG. 2 is back view of an embodiment of the anesthesia equipment lift invention positioned in storage underneath a table.
Figure 3:
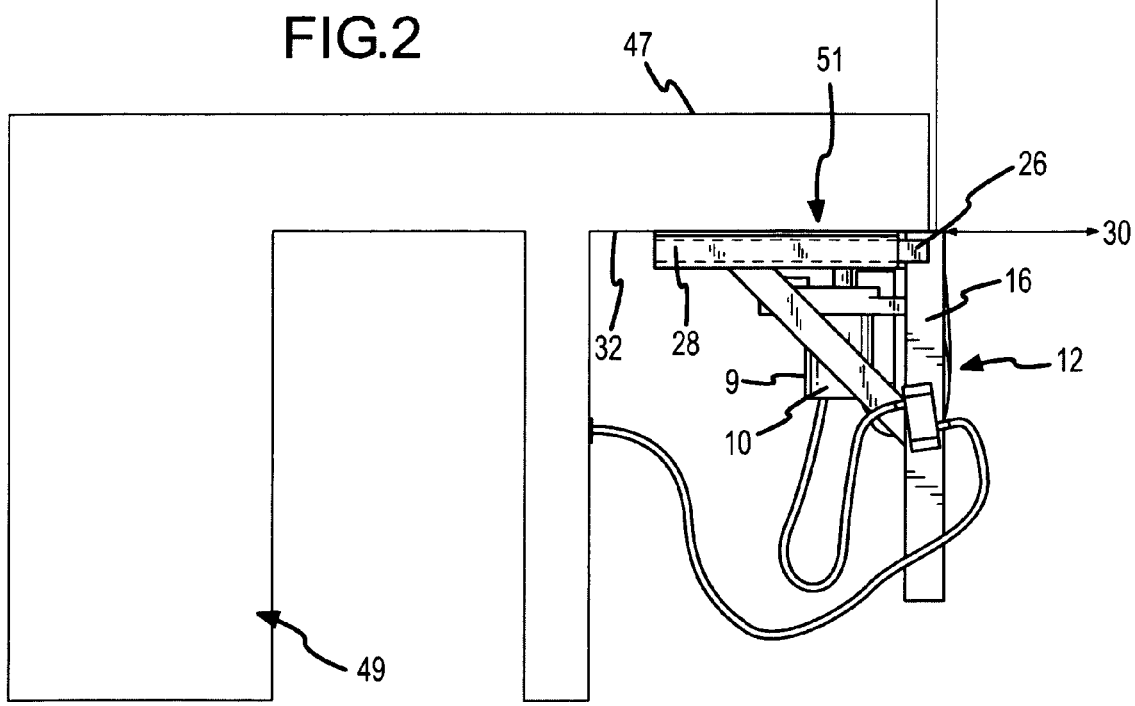
FIG. 3 is a side view of an embodiment of the anesthesia equipment lift invention positioned in storage underneath a table.

Now referring primarily to FIGS. 1-3, the inventive anesthesia lift (12) can further include a vertical frame (15) which as to certain embodiments of the inventive anesthesia lift (12) can take the form of a pair of vertical frame members (16)(17) disposed a distance apart. The lift panel (13) can be slidely coupled to the vertical frame (15), and with respect to the particular embodiment of the invention shown by FIGS. 1-3, can be slidely coupled between the pair of vertical frame members (16)(17) to allow vertical travel (18) of the lift panel (13). However, this particular embodiment of the vertical frame (15) is not intended to be limiting with respect to the various constructional forms of the vertical frame (15) which can be slidely coupled with the lift panel (13) to allow vertical travel of the lift panel (13). Vertical travel of the lift panel (13) is to be understood as the typical direction of travel which can be substantially at a right angle to the horizontal frame member (26) of the anesthesia lift (12) as further described herein. However, as to certain embodiments of the inventive anesthesia lift (12), the vertical frame (15) may allow the lift panel (13) to travel at an angle which is greater or lesser than perpendicular to the horizontal member (26) so long as travel at such angle allows height adjustment of the lift panel (13) relative to top surface (47) of the table (49) to which the anesthesia lift (12) couples. Additionally, the term slidely coupled is not intended to limit the manner in which the lift panel (13) engages the vertical frame (15) so long as the panel can move or travel vertically or at such angle which allows adjustment of lift panel (13) height relative to the top surface (47) of the table (49).

In the particular embodiment of the inventive anesthesia lift (12) shown by FIGS. 1-3, the lift panel (13) can be configured as a rectangular volume having four sides with two opposed sides of greater length (19)(20) slidely coupled to a corresponding one each of the pair of vertical frame members (16)(17). As to the embodiment of the lift (12) shown, the lift panel (13) and the pair of vertical frame members (16)(17) can be fabricated from rectangular metal tube; however, other types of material, such as plastic, and other configurations can be utilized to provide the lift panel (13) with surfaces which can be slidely coupled to the vertical frame (15).

Each of the two opposed sides of greater length (19)(20) of the lift panel (13) can provide a lift element channel (21) which mates with a corresponding one each vertical member channel insert (22) to allow vertical travel of the lift panel (13) between the pair of vertical frame members (16)(17). Understandably, the lift panel (13) could have numerous and varied configurations and the illustrative examples provided are not intended to limit the various configurations of the lift element (13) which can be utilized in accordance with the invention.

Figures 6, 7:
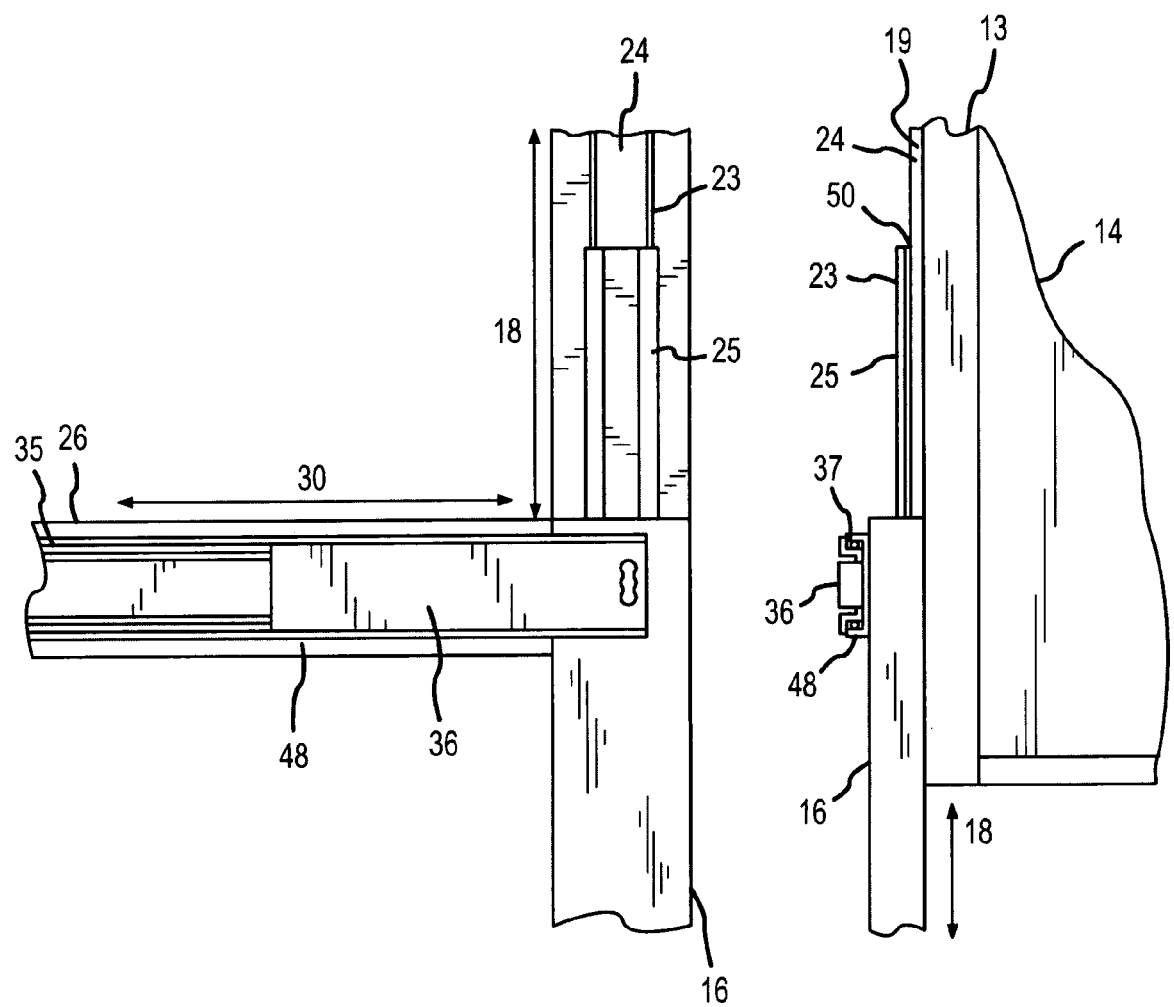
FIG. 6 is an enlarged side view of a portion of a particular embodiment of the anesthesia lift invention having discrete slide elements.
FIG. 7 is an enlarged top view of a portion of a particular embodiment of the anesthesia lift invention having discrete slide elements.

As to one particular embodiment of the inventive lift (12) shown primarily by FIGS. 6-7, a discrete slide element (23) can be coupled between each one of the vertical frame members (16)(17) and each one of the corresponding opposed sides of greater length (19)(20) of the lift panel (13) to allow the lift panel (13) to travel vertically. Each discrete slide element (23) can include a lift panel channel (24) and a vertical member channel (25) which slidely engage. A vertical slide element friction reduction assembly (50), such as a ball bearing assembly, can be located between the lift panel channel (24) and the vertical member channel (25) to provide smooth vertical travel of the lift element (14).

Again referring primarily to FIGS. 1-3 and 5, the anesthesia equipment lift (12) can further include a horizontal frame (51) which as to certain embodiments can comprise a pair of horizontal frame members (26)(27) each of which can connect to a corresponding one of the vertical frame members (16)(17). As to certain embodiments of the inventive anesthesia lift (12), the horizontal frame (51) can be coupled directly to the underside table surface (32) at a location which allows the lift panel (13) to travel vertically without travel in the horizontal frame (51). In addition, each of the pair of horizontal frame members (26)(27) can be slidely coupled to a corresponding one each of a pair of table mounts (28)(29) allowing the lift element (14) to travel a distance horizontally (30) by extending and retracting the pair of horizontal frame members (26)(27). In the particular embodiment of the invention shown, the pair of table mounts (28)(29) can be configured as metal angles each with a first leg (31) coupled to the underside table surface (32) and a second leg (33) providing a table mount surface (34) configured to slidely couple to the corresponding one of the pair of horizontal frame members (26)(27).

As shown primarily in FIGS. 6 and 7, a discrete horizontal slide element (48) can be mounted between each of the pair of table mounts (28)(29) and each of the corresponding horizontal frame members (26)(27). One configuration of a discrete horizontal slide element (48) can comprise a horizontal frame member channel (35) can be coupled to each of the pair of horizontal frame members (26)(27) and a table mount channel (36) can be coupled to each of the corresponding pair of table mounts (28)(29). The table mount channel (36) and the horizontal frame member channel (35) can be configured to slidely couple to allow extension and retraction (30) of each of the pair of horizontal frame members (26)(27). A horizontal slide element friction reduction element (37) can be further included to allow smooth operation during extension and retraction of the pair of horizontal frame members (26)(27).

Now referring primarily to FIGS. 2, 4A, 4B and 5, an elevation assembly (38) operates to generate vertical travel (18) (shown also in FIG. 3) in the lift panel (13). The elevation assembly (38) can include an elevator element (39) having first end (40) and a second (41) which can be disposed at a selectably variable distance apart (such as a hydraulic or pneumatic cylinder). The first end (40) can be coupled directly (for example by mated spiral thread, mechanical fastener, or the like) or indirectly (for example by a cord engaged by a pulley, or the like) to the lift element (14) and the second end (42) can have a fixed location by connection to the vertical frame (15). Upon operation of the elevation assembly (38), such as operation of a hydraulic or pneumatic cylinder, the first end (40) extends or retracts generating vertical travel (18) of the lift panel (13).

Figure 4A:
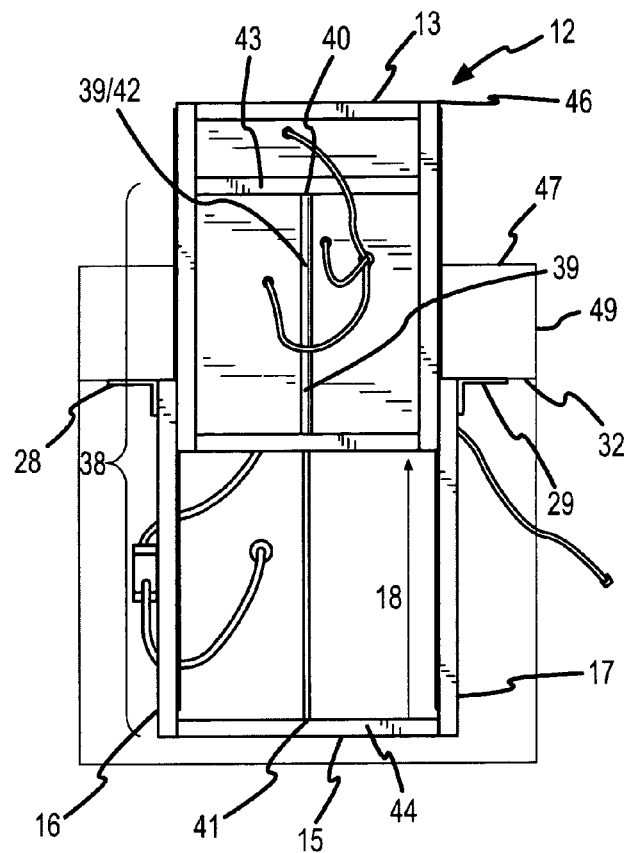
FIG. 4A is a back view of an embodiment of the anesthesia equipment lift invention positioned to provide inhalation anesthesia to a patient located on the table surface.
Figure 4B:
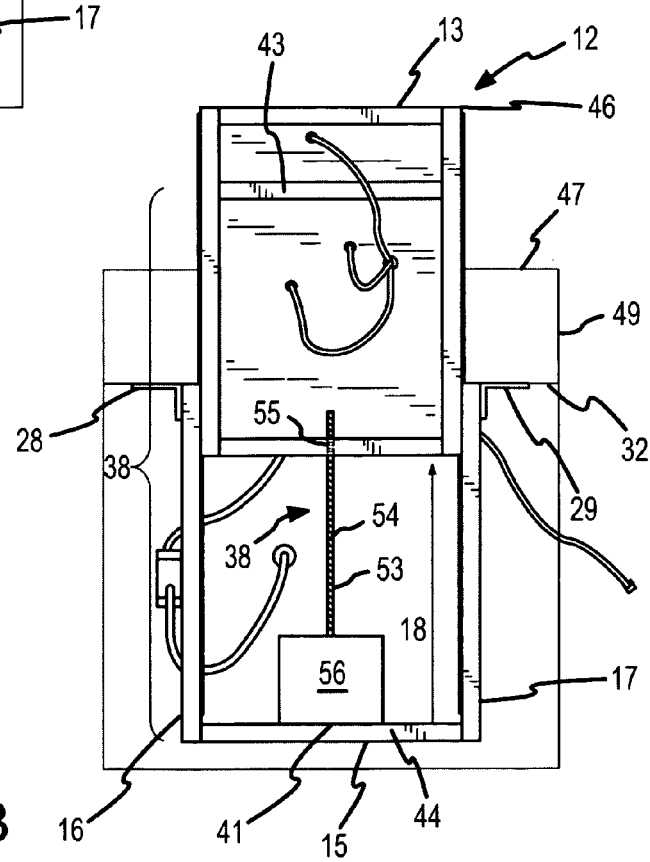
FIG. 4B is a back view of an embodiment of the anesthesia equipment lift invention positioned to provide inhalation anesthesia to a patient located on the table surface.

Also shown in FIG. 4B, as an additional example, the elevator element (38) can comprise a rotationally driven shaft (53)(driven directly or indirectly by a motor (56) as shown or manually) having a spiral thread (54) which mates with a rotationally fixed spiral thread (55) coupled to the lift panel (13). Upon operation, the spiral thread (54) of the driven shaft (53) rotationally engages the rotationally fixed spiral thread (55) coupled to the lift element (14) to generate vertical travel (18) in the lift panel (13).

The elevation assembly (38) of a preferred embodiment of the inventive anesthesia equipment lift (12)(shown primarily by FIG. 4) comprises a pneumatic cylinder (42) having a first end (40) directly coupled to a lift cross member (43) connected to opposed sides (19)(20) of the lift element (14) and a second end (41) having fixed location on a vertical frame cross member (44). Extension and retraction of the first end (40) of the pneumatic cylinder (42) generates vertical travel in the lift cross member (43) and a corresponding amount of vertical travel (18) of the lift panel (13).

Figure 5:
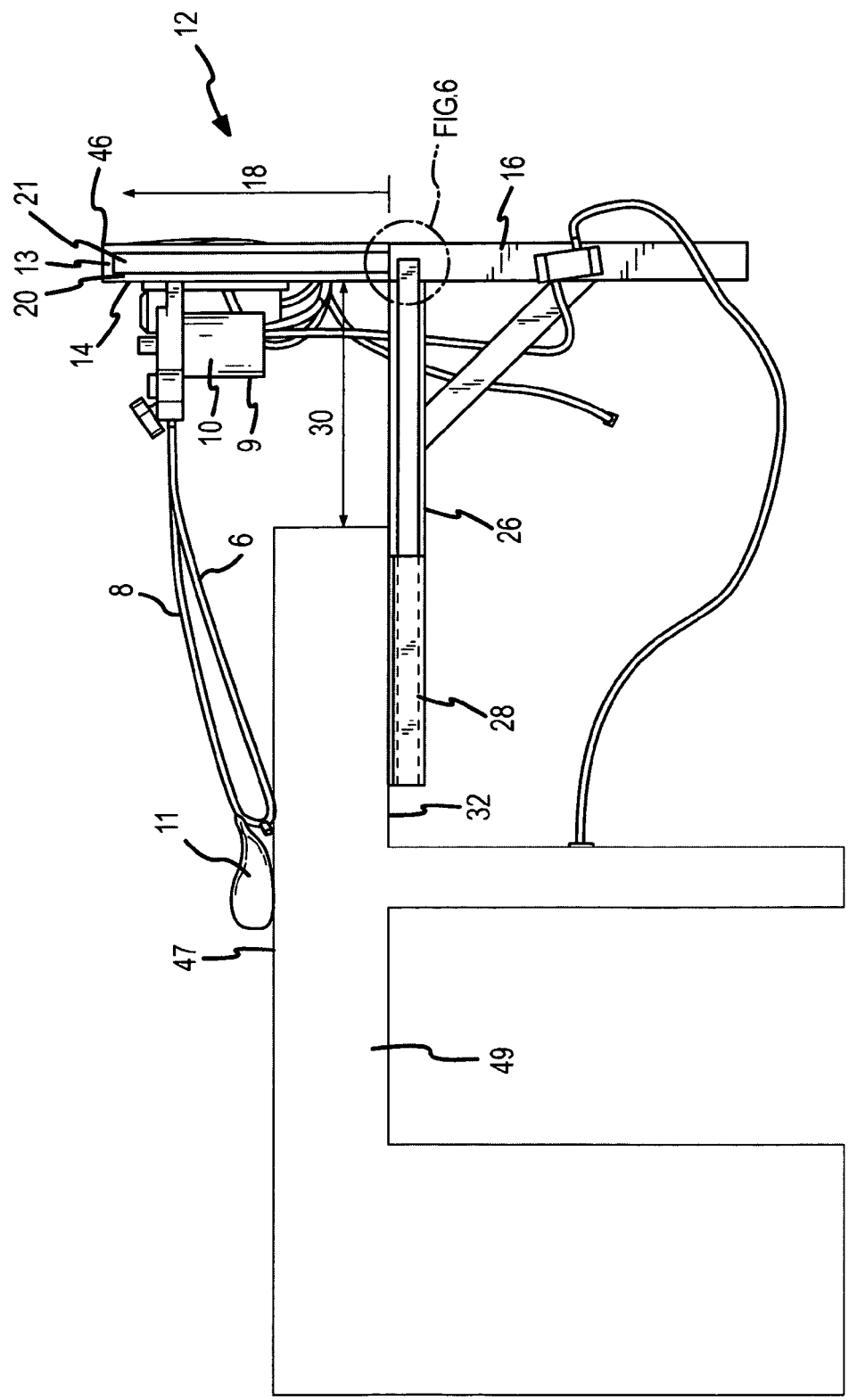
FIG. 5 is a side view of an embodiment of the anesthesia equipment lift invention positioned to provide inhalation anesthesia to a patient located on the table surface.

Now referring primarily to FIGS. 2, 3 and 5, the lift panel (13) can travel vertically (18) to be positioned at a first location (45) allowing the horizontal frame members (26)(27) to travel a sufficient horizontal distance (30) to position the lift element (13) beneath the underside table surface (32). As shown primarily by FIGS. 1 and 4, to utilize the anesthesia equipment mounted to the lift mount surface (14), the horizontal frame members (26)(27) can travel a sufficient horizontal distance (30) to allow operation of the elevation assembly (38) to generate vertical travel (18) of the lift element (13) to the second location (46)(shown by FIGS. 4 and 5) which positions mounted inhalation anesthesia equipment proximate to a patient (not shown) located on the table surface (47) to perform inhalation anesthesia.

As can be easily understood from the foregoing, the basic concepts of the present invention may be embodied in a variety of ways. The invention involves numerous and varied embodiments of an anesthesia equipment lift system and methods of making and using such anesthesia lift system.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "elevator" should be understood to encompass disclosure of the act of "elevating"—whether explicitly discussed or not—and, conversely, were there effectively disclosure of the act of "elevating", such a disclosure should be understood to encompass disclosure of a "elevator" and even a "means for elevating." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the anesthesia equipment lifts herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below, if any, are intended describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A method of positioning an anesthesia device, comprising the steps of:
 a. mounting at least a part of said anesthesia device to a lift panel having a pair of opposed faces and a pair of opposed outer sides;
 b. slidely coupling said lift panel between a pair of vertical frame members by opposed outer sides, each of said pair of vertical frame members correspondingly coupled to a horizontal frame member, each said horizontal frame member slidely coupled to the bottom surface of a treatment table;

b. generating horizontal travel in said lift panel by slidely extending each said horizontal frame member from a first location beneath said bottom surface of said treatment table to a second location which allows vertical travel in said lift panel; and c. generating vertical travel in said lift panel by sliding said lift panel between said pair of vertical frame members from said second location to a third location which positions said part of said anesthesia device facing said treatment table at a height greater than the top surface of said treatment table.

2. The method as described in claim 1, further comprising the step of generating vertical travel in said lift panel from said third location to said second location.

3. The method as described in claim 2, further comprising the step of generating horizontal travel in said lift panel from said second location to said first location.

4. The method as described in claim 3, wherein generating vertical travel in said lift panel between said vertical members further comprises the step of operating an elevation assembly coupled to said lift panel.

5. The method as described in claim 4, wherein said step of operating an elevation assembly coupled to said lift panel comprises the step of operating a pneumatic cylinder having a first end coupled to said lift panel and a second end fixed at a location, and wherein operating said pneumatic cylinder selectably varies distance between said first end and said second end.

6. The method as described in claim 4, wherein said step of operating an elevation assembly coupled to said lift panel comprises the step of rotating a rod having a spiral thread mated with a spiral thread coupled to said lift panel.

7. A method of assembling a lift for positioning an anesthesia device, comprising the steps of:

a. slidely coupling a lift panel by opposed outer sides between a pair of vertical frame members to provide a front surface for mounting said anesthesia device;

b. coupling said pair of vertical frame members to a corresponding pair of horizontal frame members, wherein said pair of horizontal frame members allow horizontal travel of said pair of vertical frame members;

c. coupling each of said pair of horizontal frame members to a bottom table surface of a treatment table at a location which allows said lift panel coupled between said pair of vertical frame members to travel to a position beneath said treatment table.

8. The method of assembling a lift for positioning an anesthesia device as described in claim 7, further comprising the step of coupling an elevation assembly to said lift panel, and wherein operation of said lift assembly generates vertical travel in said lift panel between said vertical frame members.

* * * * *